US00PP34689P2

(12) United States Plant Patent
Hansen

(10) Patent No.: US PP34,689 P2
(45) Date of Patent: Oct. 25, 2022

(54) ***BAPTISIA* PLANT NAMED 'BURGUNDY BLAST'**

(50) Latin Name: ***Baptisia* hybrid**
Varietal Denomination: Burgundy Blast

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,085

(22) Filed: Feb. 1, 2022

(51) Int. Cl.
*A01H 5/02* (2018.01)
*A01H 6/54* (2018.01)

(52) U.S. Cl.
USPC ..... Plt./263.1
CPC ..... *A01H 6/54* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct plant cultivar of hardy herbaceous False Indigo plant named *Baptisia* 'Burgundy Blast' characterized by flowers that open up dark wine-purple beginning in late May and continuing for two weeks. The new plant has a narrow, medium height, upright, vase-shaped, multi-stemmed, winter-hardy habit with glaucous dark-green tri-foliate foliage and is suitable for landscaping as a specimen or en masse.

2 Drawing Sheets

Botanical classification: *Baptisia* hybrid.
Cultivar designation: 'Burgundy Blast'.

STATEMENT REGARDING PRIOR DISCLOSURES UNDER 37 CFR 1.77(B)(6)

*Baptisia* 'Burgundy Blast' was promoted in a non-enabling descriptions and photographs on a website operated by Walters Gardens, Inc. on Feb. 1, 2021, followed by the "Walters Gardens 21-22 Catalog" initially distributed by Walters Gardens, Inc. on May 21, 2021. The first enabling disclosure of *Baptisia* 'Burgundy Blast', in the form of a sale, was made by Walters Gardens, Inc. on May 17, 2021 to Phoenix Perennials, Monrovia Nursery, Wildflower Farms and Renegade Acres. Information and plants for this sale and all sales thereafter were obtained from the inventor. No plants of *Baptisia* 'Burgundy Blast' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Burgundy Blast' and will be referred to hereafter by its cultivar name, 'Burgundy Blast', and the new plant. The new plant represents a new false indigo, a hardy herbaceous perennial grown for landscape and cut flower use.

'Burgundy Blast' arose from an ongoing breeding program of the inventor at a wholesale perennial nursery in Zeeland, Mich. with the specific intention of improving garden worthiness of perennial false indigo plants with a wider variety of flower colors and improved garden habit.

*Baptisia* 'Burgundy Blast' was a single seedling selection from a cross between a proprietary unnamed, unreleased hybrid selection of *Baptisia minor* (not patented) as the female or seed parent times a proprietary unnamed, unreleased hybrid selection of *Baptisia alba* (not patented) as the male or pollen parent. The cross was performed at the same nursery in Zeeland, Mich. with the seeds collected on Aug. 23, 2011. The seeds were then sown the same nursery in Zeeland, Mich. on Oct. 6, 2011. The initial selection made in the spring of 2013 at the same nursery in Zeeland and later given the breeder code 11-11-11.

'Burgundy Blast' was initially asexually propagated by stem cuttings at a wholesale perennial nursery in Zeeland, Mich. in 2015. The resultant plants have demonstrated that the new plant has remained stable and true to type in successive generations of asexual propagation.

The nearest comparison plants known to the inventor are: 'Grape Taffy' U.S. Plant Pat. No. 26,587, 'Pink Truffles' U.S. Plant Pat. No. 26,588, 'Violet Dusk' U.S. Plant Pat. No. 32,553, 'Lavender Stardust' (not patented) and 'Plum Rosy' U.S. Plant patent application Ser. No. 17/300,370.

'Grape Taffy' is much shorter and more compact in habit and the flowers are reddish-purple with a buff-yellow keel. 'Pink Truffles' is taller and broader in habit with soft pink flowers having a yellow keel. 'Violet Dusk' is slightly taller in height and width and the flowers are lavender-violet with cream-colored keels. 'Lavender Stardust' has a taller vase-shaped habit, but the flowers have a pale-yellow keel with the lilac-purple banner, and the inflorescence is much longer. 'Plum Rosy' has a slightly larger habit and flowers that open a soft-yellow and turn to a dusty raspberry-purple.

Compared with plants of *Baptisia minor* known to the Inventor, the new plant is taller in habit and has a longer inflorescence. Typical *Baptisia alba* typically has white flowers. The female parent has blue flowers on a more compact plant and the inflorescence is longer. The male parent has a similar habit, but the flowers are pure white, later opening, the inflorescences are longer and the peduncles are light green.

The new plant differs from all *Baptisia* known to the inventor in the following combined traits:

1. Flowers open dark wine-purple and retain their color through the effective season;
2. Flowering begins late-May in Michigan and continues for about two weeks;
3. Narrow, medium-height, upright, vase-shaped, multi-stemmed, winter-hardy habit;
4. Glaucous, dark-green, tri-foliate foliage.

BRIEF DESCRIPTION OF THE DRAWINGS

The photographs of 'Burgundy Blast' demonstrate the unique traits of the new plant and the overall appearance. The colors are as accurate as reasonably possible with color reproductions. Variation in ambient light spectrum, source and direction may cause the appearance of minor variation in color. The accompanying photograph is of a six-year-old plant growing in an open full-sun trial garden in Zeeland, Mich.

DETAILED BOTANICAL DESCRIPTION OF THE PLANT

Figure 1:
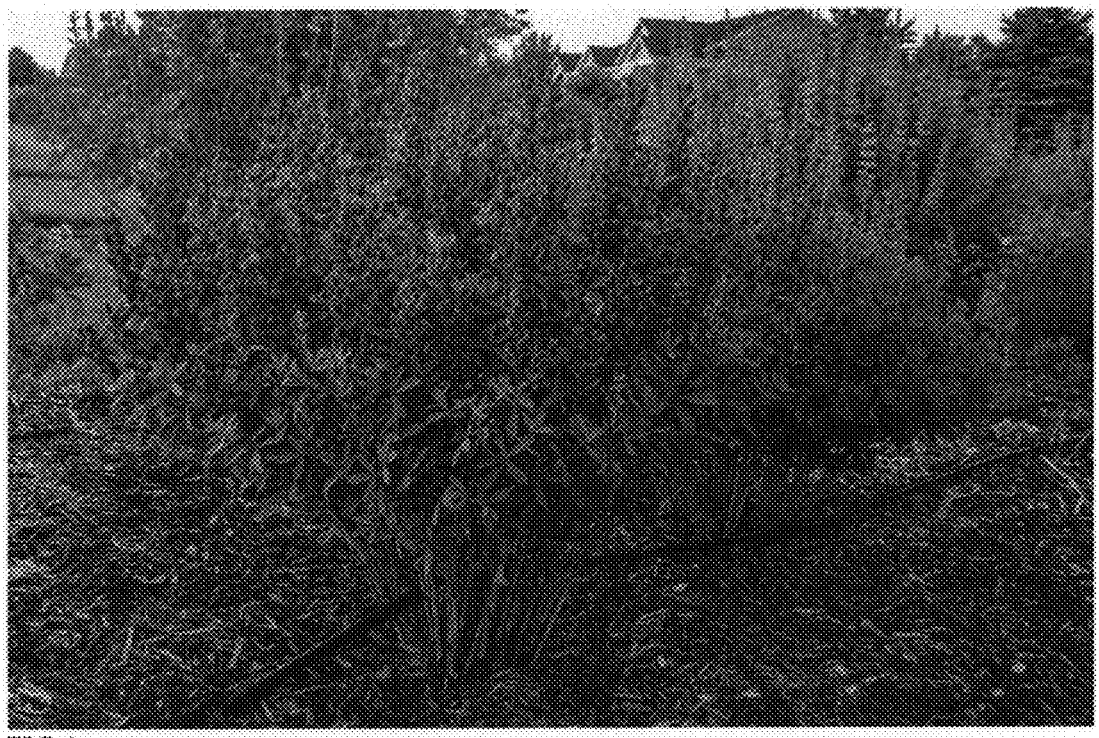
FIG. 1 shows the habit of a plant in full flower.
Figure 2:
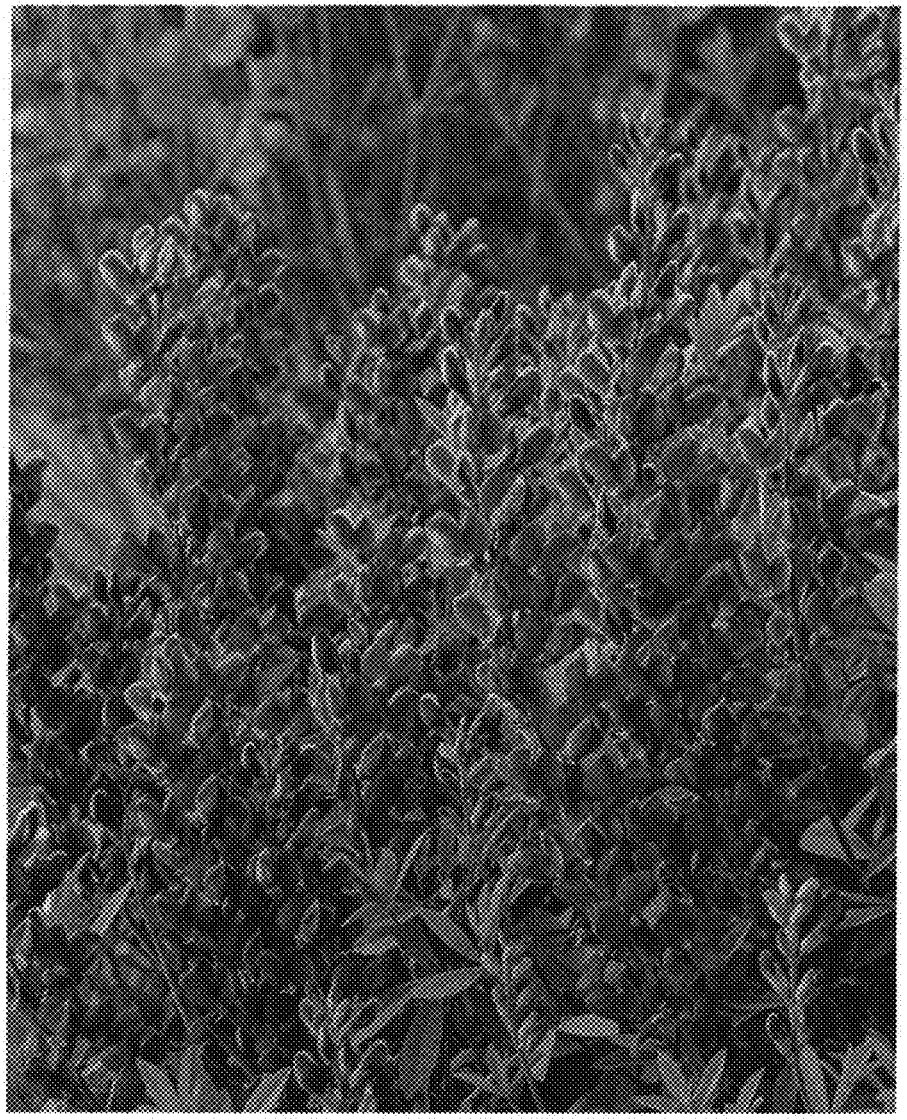
FIG. 2 shows a close-up of the inflorescence.

The following is a detailed description of six and ten-year-old plants of 'Burgundy Blast' as grown outdoors in a trial block at a wholesale perennial nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 28 cm across at soil level, at flowering about 76 cm tall from soil to top of flowers and 94 cm wide just below initial flowers; at maturity plant foliage height about 105 cm tall and about 108 cm wide;

Roots: Fibrous, well-branched, long, deeply rooted;

Root color: Nearest RHS 161D;

Propagation method: Stem cuttings, rooting in about three weeks;

Growth rate: Moderate to average;

Stems: Rigid and upright; highly glaucous; glabrous; cylindrical with shallow longitudinal furrows; lower two to three nodes without leaves or branches; normally two to three branches per plant below flowers; about 60 stems per clump;

Stem size: Main stem to about 9 mm diameter at base and 105 cm tall, average about 96 cm long and about 8 mm diameter; to about 48 cm long from soil to below initial flowers;

Stem branches: Primary branches at 45 to 60-degree angle above horizontal, up to 30 cm long and 5 mm diameter, average for primary branches about 24 cm long and 4 mm diameter, smaller distally; and two to four alternate secondary branches per stem of about 16 cm long and 3 mm diameter, averaging about 12.5 cm long and 3 mm diameter;

Stem color: Variable, nearest RHS N77C, and between RHS 138A and RHS 194B;

Stem scales: At stem nodes; lanceolate; emarginate to retuse apex with sharply pointed sides; truncate clasping base; margin entire; dehiscing to leave behind thin scar on stem; about 18 mm wide at base and 21 mm wide in center; about 28 mm long and 2 mm wide in center of apex; Stem scale color: variable, nearest RHS N186A, RHS 148C and between RHS 146B and RHS 147B before dehiscing;

Internodes: Up to 13 cm apart between lowest branches, average about 9 cm;

Internode color: Between RHS 138D and RHS 148D with frequent marks of nearest RHS N186A;

Foliage: Alternate; ternate to palmately compound with three leaflets; outer two leaflets independent, at nearly 90-degree angle to middle leaflet; up to 7 cm long and 9.5 cm wide;

Leaflet: Three; oblanceolate; apex acute, base cuneate; margins entire; petiolate; adaxial and abaxial surfaces matte, glabrous; slightly glaucous adaxial and glaucous abaxial; middle lobe to about 5.2 cm long and 2 cm wide, side lobes about 4.8 cm long and 1.8 cm wide;

Leaflet color: Newly expanding adaxial nearest RHS 146B with a light blush concentrated around margin of nearest RHS N186C, abaxial nearest RHS 147C; mature adaxial nearest RHS N138B, abaxial nearest RHS 147B;

Venation: Pinnate, glabrous, thin, not conspicuous;

Vein color: Newly expanding foliage adaxial midrib nearest RHS 138B and abaxial nearest RHS 147C; mature adaxial midrib nearest RHS 138C and secondary veins nearest RHS N138B, abaxial midrib lighter than RHS 145D and secondary veins same nearest RHS 147B;

Petioles: Glabrous; slightly glaucous; cylindrical; to about 6 mm long and 2 mm wide at base, average 5 cm long and 1.5 mm wide;

Petiole color: Adaxial nearest 146D, abaxial nearest RHS 147B;

Stipules: Narrowly lanceolate, acute apex with base truncate; to about 22 mm long and 8 mm wide, average 20 mm long and 6 mm wide with largest stipules below primary branches and decreasing distally and on secondary branches;

Stipule color: Nearest RHS 138A both surfaces;

Peduncle: Cylindrical with vertical shallow ridges and furrows; glaucous; glabrous; from first flower to apex about 25 cm long; diameter at the base of first flower about 3.5 mm and about 2 mm diameter at the apex;

Peduncle color: Between RHS N187A and RHS N186B in the flowering portions;

Pedicel: Cylindrical, glabrous, glaucous; about 9 mm long and 1 mm diameter;

Pedicel color: Between RHS 189A and RHS N186B;

Calyx: Campanulate; four-lobed; to about 12 mm long, 9 mm tall and 11 mm across at apex;

Sepals: Four; one larger dorsal, one ventral and two lower lateral; acute apices; fused into tube in proximal 9 mm; margin entire; glabrous adaxial and abaxial; dorsal sepal to about 12 mm long and 7 mm wide at fusion; other three sepals to about 12 mm long and 4 mm across at fusion;

Sepal color: Adaxial between RHS 144B and RHS 144A with moderate distal blushing of nearest RHS N77C; abaxial nearest RHS 148B with moderate blushing of nearest RHS N77C distally;

Buds one day prior to anthesis: Oblong elliptic, flatted vertically; to about 25 mm long and 9 mm tall and 7 mm wide, slightly smaller in distal flowers;

Bud color: One day prior to opening exposed keel petal blend between RHS 79D and RHS N77D, enfolded banner petal between RHS 79D and RHS N77D, exposed alae petals between RHS 145D and RHS 150D;

Flower: Zygomorphic, papilionaceous, non-secund, held at about 45-degree angle above horizontal; about 33 flowers per main raceme and about 12 per secondary branch; seasonally effective for about 2 weeks beginning in late May in Zeeland, Mich.; individual flowers remain effective and on raceme for about four days; individually to about 26 mm long, 17 mm tall and 18 mm wide at largest portions; consisting of an upper banner, a lower keel made up of two lobes folded around gynoecium and androecium; and two lateral wings or alae laterally appressed against keel;

Flower fragrance: None detected;

Petals: Five; with a lower fused keel, an upper banner, and two lateral wings or alae; keel comprised of two sections that are folded around stamens and pistil;

*Banner petal*.—Conduplicate, reflexed upward and backward and pinched in the middle; apex retuse, base claw-like, margin entire; to about 22 mm long, 12 mm across natural width, 21 mm wide flattened spread and 8 mm tall; with rounded emarginate apex notched about 4 mm deep; basal portion attenuate claw-type, 5 mm long and 3 mm wide.

*Banner color*.—Adaxial between RHS N77B and RHS 79D with claw base nearest RHS 145C; abaxial between RHS N80D and RHS N79D, center nearest RHS N77D with claw nearest RHS 145C.

*Keel*.—Comprised of two main lobes that are folded around stamens and pistil; fused in the distal one-third with the apex emarginate or retuse and the bases separate and claw-like; margin entire; top edge about one-third of the way from base has 2 mm smaller lobe pointing toward base; about 23.5 mm long and 11 mm tall and 2 mm wide; blade portion to about 18 mm long and 10 mm tall, with claw to about 7.5 mm long and base narrowed to 2 mm wide for the proximal 3 mm.

*Keel color*.—Adaxial base nearest RHS 145D, dorsally nearest RHS N77B and ventrally nearest RHS 11D; abaxial keel ventral portion between RHS 158D and RHS 11D and dorsal portion RHS N77B, base nearest RHS 145D;

*Alae*.—Two; papilionaceous corolla appendage with rounded apex and claw-like base; with 2 mm long by 2 mm wide lobe pointing toward base and about one-third of the way from base; about 23 mm long and 10 mm tall with the claw to 3 mm wide at base of blade and 2 mm wide at base and 8 mm long; blade about 14 mm long and 10 mm wide.

*Alae color*.—Adaxial claw base nearest RHS 145D; main blade portion and lobe nearest RHS N77D; abaxial claw base nearest RHS 145D, small lobe and main lobe portion nearest RHS 145D.

*Mature keel and upper banner*.—Between RHS N77B and RHS 79D.

Receptacle: Disk-shaped, about 4 mm diameter and 1.2 mm depth; color nearest RHS 138A;

Gynoecium: One, with superior ovary and stipe; to about 23 mm long;

*Style*.—Cylindrical; glabrous; slightly glaucous; tapered and curved near stigma, about 9 mm long and about 0.7 mm diameter above ovary; color between RHS 150D and RHS N144D.

*Stigma*.—About 0.2 mm diameter; color nearest RHS 150D.

*Ovary*.—Superior above hypanthium, suspended by stipe; about 7 mm long and about 1.5 mm in diameter; color between RHS 150D and RHS N144D.

*Stipe*.—Cylindrical; glabrous; slightly glaucous; about 5 mm long and 0.7 mm diameter; color between RHS 150D and RHS N144D.

Androecium:

*Stamens*.—Ten.

*Filament*.—Glabrous; slightly lustrous; not united 21 mm in length and about 0.5 mm in diameter; slightly curved upward distally; color nearest RHS 150D.

*Anther*.—Dorsifixed, oblong; about 2.0 mm long and 1 mm wide; color nearest RHS 17A.

*Pollen*.—Spherical; abundant; color nearest RHS 17A.

Fruit: Bivalve inflated ellipsoidal pod; glabrous; about 33 mm long, 20 mm across and 14 mm thick; with thin, linear, arcuate, terminal beak about 3.0 mm long and about 1 mm thick; rounded base, Fruit color: At maturity between 200A and RHS 202A;

Seeds: About 8 per pod (open pollinated); reniform; glabrous; about 4 mm long, 3 mm across and 2 mm thick; color nearest RHS N199C;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed.

It is claimed:

1. A new and distinct cultivar of *Baptisia* plant named 'Burgundy Blast' as herein described and illustrated.

* * * * *